United States Patent
Dellamorte et al.

(10) Patent No.: US 12,330,140 B2
(45) Date of Patent: Jun. 17, 2025

(54) CATALYST COMPOSITIONS AND METHODS OF PREPARATION AND USE THEREOF

(71) Applicants: BASF CORPORATION, Florham Park, NJ (US); THE REGENTS OF THE UNIVERSITY OF CALIFORNIA, Oakland, CA (US)

(72) Inventors: Joseph C. Dellamorte, Beachwood, OH (US); Enrique Iglesia, Berkeley, CA (US); Teng Fu, Shanghai (CN); Biswanath Dutta, Berkeley, CA (US)

(73) Assignees: BASF CORPORATION, Florham Park, NJ (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 218 days.

(21) Appl. No.: 17/800,803

(22) PCT Filed: Feb. 8, 2021

(86) PCT No.: PCT/US2021/017072
§ 371 (c)(1),
(2) Date: Aug. 18, 2022

(87) PCT Pub. No.: WO2021/173333
PCT Pub. Date: Sep. 2, 2021

(65) Prior Publication Data
US 2023/0090704 A1    Mar. 23, 2023

Related U.S. Application Data

(60) Provisional application No. 62/981,655, filed on Feb. 26, 2020.

(51) Int. Cl.
| | |
|---|---|
| *B01J 21/06* | (2006.01) |
| *B01J 23/10* | (2006.01) |
| *B01J 35/50* | (2024.01) |
| *B01J 35/51* | (2024.01) |
| *B01J 35/61* | (2024.01) |
| *B01J 37/18* | (2006.01) |
| *C01G 25/02* | (2006.01) |
| *C07C 5/333* | (2006.01) |

(52) U.S. Cl.
CPC ............ *B01J 21/066* (2013.01); *B01J 23/10* (2013.01); *B01J 35/50* (2024.01); *B01J 35/51* (2024.01); *B01J 35/612* (2024.01); *B01J 35/613* (2024.01); *B01J 35/615* (2024.01); *B01J 37/18* (2013.01); *C01G 25/02* (2013.01); *C07C 5/3332* (2013.01); *C01P 2002/76* (2013.01); *C01P 2006/12* (2013.01); *C07C 2521/06* (2013.01)

(58) Field of Classification Search
CPC . B01J 21/066; B01J 23/10; B01J 35/51; B01J 35/612; B01J 35/613; B01J 35/615; B01J 35/50; B01J 37/18; C01P 2006/12; C01P 2002/76; C01P 2004/61; C01P 2004/60; C01P 2004/32; C01P 2004/50
USPC .................................................. 502/302, 349
See application file for complete search history.

(56) References Cited

U.S. PATENT DOCUMENTS

| | | | | |
|---|---|---|---|---|
| 5,908,807 | A * | 6/1999 | Vanderspurt | B01J 23/38 502/343 |
| 6,576,804 | B1 * | 6/2003 | Heineke | C07C 5/3332 585/662 |
| 7,569,512 | B2 * | 8/2009 | Weissman | B01J 37/0215 502/325 |
| 7,994,090 | B2 * | 8/2011 | Beppu | B01J 37/08 502/202 |
| 2005/0119515 | A1 | 6/2005 | Machhammer et al. | |
| 2006/0270881 | A1 | 11/2006 | Dakka et al. | |
| 2009/0325791 | A1 | 12/2009 | Pan et al. | |
| 2013/0079566 | A1 | 3/2013 | Lin | |
| 2015/0375202 | A1 | 12/2015 | Nagao et al. | |

FOREIGN PATENT DOCUMENTS

| | | |
|---|---|---|
| CN | 1261360 C | 7/2000 |
| CN | 1524794 A | 9/2004 |

OTHER PUBLICATIONS

European Search Report of European Application No. 21760014.7 mailed Feb. 27, 2024, 8 pgs.
International Search Report and Written Opinion of International Application No. PCT/US2021/017072 mailed Jul. 15, 2021, 18 pgs.
Otroshchenko, et al., " Non-oxidative dehydrogenation of propane, n-butane, and isobutane over bulk ZrO2-based catalyst: Effect of dopant on active site and pathways of produce formation", Catalysis Science & Technology, Aug. 30, 2017, vol. 00, No. 1-3, 12 pages.

* cited by examiner

*Primary Examiner* — Patricia L. Hailey
(74) *Attorney, Agent, or Firm* — Lowenstein Sandler LLP

(57) ABSTRACT

Disclosed are methods of dehydrogenating a light alkane gas (and/or light alkene gas), which include adding hydrogen ($H_2$) to the light alkane gas (and/or light alkene gas) in the presence of a catalyst composition containing zirconium oxide. Also disclosed are catalyst compositions containing zirconium oxide and methods of preparation thereof, where the catalyst compositions are useful in methods of dehydrogenating light alkane gas.

15 Claims, 4 Drawing Sheets

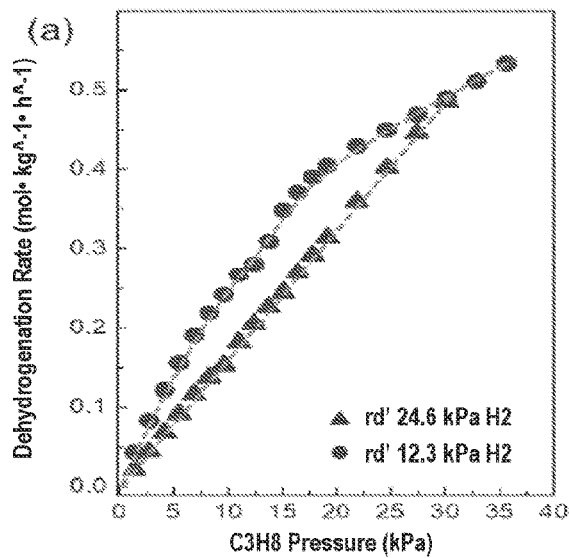
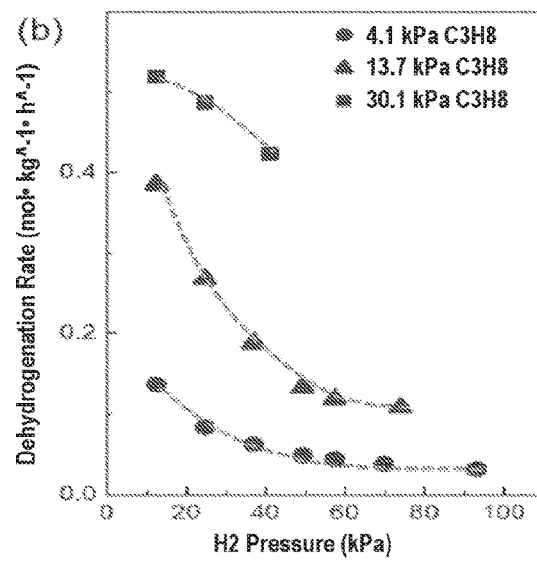
FIG. 7A
FIG. 7B
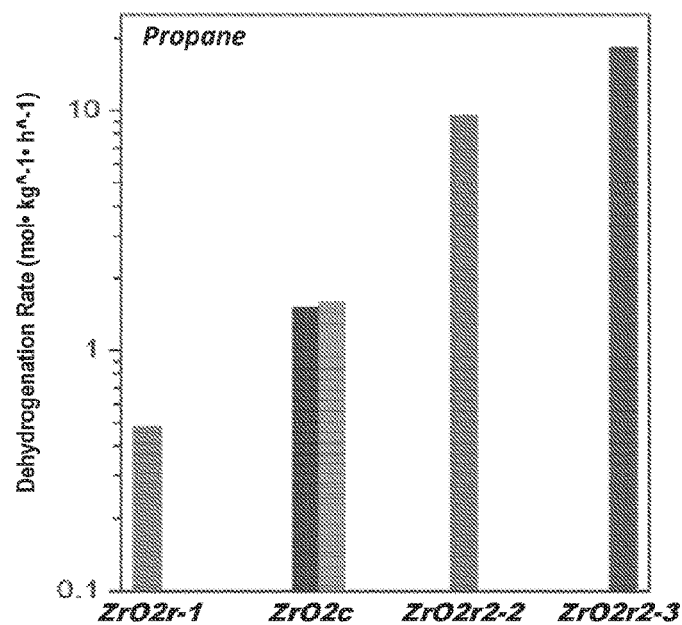
FIG. 8

CATALYST COMPOSITIONS AND METHODS OF PREPARATION AND USE THEREOF

CROSS-REFERENCE TO RELATED APPLICATIONS

The present application is a national stage entry under 35 U.S.C. § 371 of International Patent Application No. PCT/US2021/017072, filed on Feb. 8, 2021, which claims the benefit of priority of U.S. Provisional Patent Application No. 62/981,655, filed on Feb. 26, 2020, the disclosures of which are hereby incorporated by reference herein in their entireties.

FIELD

This disclosure relates to methods of using catalyst compositions for dehydrogenation of light alkane gas (and/or light alkene gas). The disclosure also relates to catalyst compositions, for example, that can be used in such dehydrogenation reactions and methods of preparation thereof.

BACKGROUND

Catalytic dehydrogenation of alkanes is an efficient conversion technology for the production of alkenes as compared to traditional petroleum-based processes such as fluid catalytic cracking and thermal steam cracking. Traditional processes suffer from high-energy demand, dwindling petroleum reserve and low selectivity toward any particular target alkene. Catalytic dehydrogenation is also more environmentally friendly than oil-based processes because it uses natural gas and shale gas as feedstock, which contain fewer impurities.

Two industrial processes for the production of light alkene using dehydrogenation are 1) the chromia-alumina-based Catofin® process; and 2) the Pt—Sn-based Oleflex™ process. However, the use of chromium (Cr) and platinum (Pt) based catalysts presents environmental and health issues. For example, according to the Occupational Safety and Health Administration (OSHA), human exposure to chromium (VI) ($Cr^{6+}$) may cause serious health issues such as lung cancer.

Platinum-based catalysts used for dehydrogenation of alkanes can include Pt deposited alone, or in combination with another material such as tin (Sn), on an inactive support. The inactive support can be, for example, a $ZrO_2$ support that is inactive under the reaction conditions that cause the Pt or Pt—Sn to be active. However, the re-dispersion of Pt in such catalysts often requires the addition of chlorine-based compounds during the catalyst regeneration process, which is ecologically harmful. Moreover, such Pt-based catalysts are sensitive to trace impurities and very costly.

There is a need for methods and catalyst compositions that inhibit deactivation of the catalyst composition and at same time maintain a considerable dehydrogenation activity. There is a further need for catalyst compositions that are free of Cr and precious metals, such as Pt, and that increase the safety and sustainability of the dehydrogenation process. The use of such catalyst compositions in the dehydrogenation of light alkanes (and/or alkenes) could improve the total yield of dehydrogenation products within one cycle and require less frequent catalyst regenerations.

BRIEF DESCRIPTION OF THE DRAWINGS

FIG. 7(a) shows the dehydrogenation rate per mass of catalyst ($r_d$) during a PDH reaction on a $ZrO_2$ catalyst as a function of $C_3H_8$ partial pressure.

FIG. 7(b) shows the dehydrogenation rate per mass of catalyst ($r_d$) during a PDH reaction.

FIG. 8 shows a comparison of initial dehydrogenation rate of propane among $ZrO_2$ catalysts.

BRIEF SUMMARY

Figure 1:
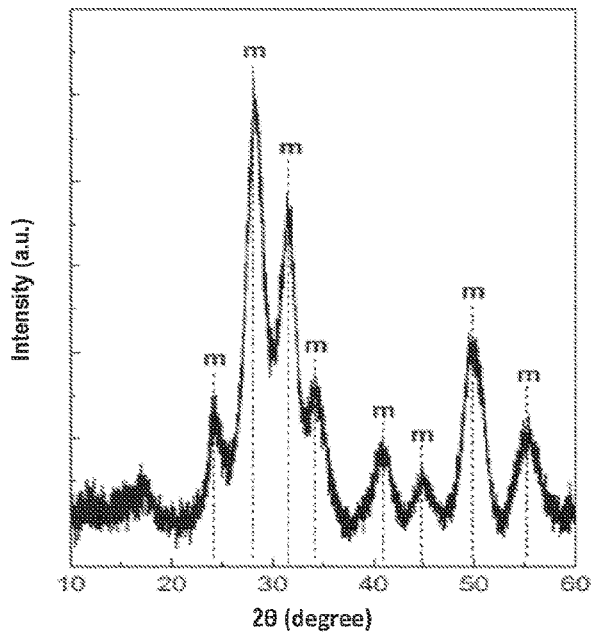
FIG. 1 shows an X-ray diffraction (XRD) spectrum of a catalyst composition comprising zirconium oxide ($ZrO_2$) according to embodiments.

According to various embodiments, disclosed herein are catalyst compositions, comprising zirconium oxide ($ZiO_2$), wherein the catalyst compositions are free of at least one of chromium and a precious metal (e.g., Pt, gold, silver, copper, palladium, etc.). In embodiments, the catalyst compositions are free of chromium and platinum.

Further disclosed herein, according to various embodiments, is a method of preparing a catalyst composition, comprising combining $ZrO(NO_3)_2 \cdot xH_2O$, water and urea at a temperature of about 20° C. to about 25° C. to form a $ZrO(NO_3)_2$ solution; and crystallizing the $ZrO(NO_3)_2$ solution at an elevated temperature under an autogenous pressure for about 2 h to about 36 h to form the catalyst composition.

According to further embodiments, disclosed herein is a method for dehydrogenating a light alkane gas (and/or a light alkene gas), comprising: combining hydrogen ($H_2$) with the light alkane gas (and/or light alkene gas) in the presence of a catalyst composition comprising zirconium oxide ($ZrO_2$).

DETAILED DESCRIPTION

Described herein are methods of using catalyst compositions for the dehydrogenation of light alkane gases (and/or light alkene gases). Also disclosed are catalyst compositions for such dehydrogenation reactions and methods of preparation thereof. It is to be understood that the invention is not limited to the details of construction or process steps set forth in the following description. The invention is capable of other embodiments and of being practiced or being carried out in a variety of ways.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

As used herein, the singular forms "a," "an," and "the" include plural references unless the context clearly indicates otherwise. Thus, for example, reference to "a catalyst material" includes a single catalyst material as well as a mixture of two or more different catalyst materials.

As used herein, the term "about" in connection with a measured quantity, refers to the normal variations in that measured quantity as expected by one of ordinary skill in the art in making the measurement and exercising a level of care commensurate with the objective of measurement and the precision of the measuring equipment. In certain embodiments, the term "about" includes the recited number 10%, such that "about 10" would include from 9 to 11.

The term "at least about" in connection with a measured quantity refers to the normal variations in the measured quantity, as expected by one of ordinary skill in the art in making the measurement and exercising a level of care commensurate with the objective of measurement and precisions of the measuring equipment and any quantities higher than that. In certain embodiments, the term "at least about" includes the recited number minus 10% and any quantity that is higher such that "at least about 10" would include 9 and anything greater than 9. This term can also be expressed as "about 10 or more." Similarly, the term "less than about" typically includes the recited number plus 10% and any quantity that is lower such that "less than about 10" would include 11 and anything less than 11. This term can also be expressed as "about 10 or less."

Unless otherwise indicated, all parts and percentages are by weight except that all parts and percentages of gas are by volume. Weight percent (wt %), if not otherwise indicated, is based on an entire composition free of any volatiles, that is, based on dry solids content. Volume percent (vol %), if not otherwise indicated, is based on the total volume of the gas.

Although the disclosure herein is with reference to particular embodiments, it is to be understood that these embodiments are merely illustrative of the principles and applications of the invention. It will be apparent to those skilled in the art that various modifications and variations can be made to the compositions and methods without departing from the spirit and scope of the invention. Thus, it is intended that the invention include modifications and variations that are within the scope of the appended claims and their equivalents.

Disclosed herein are methods of using a catalyst composition comprising zirconium oxide for dehydrogenation of light alkane gas (and/or light alkene gas) in the presence of hydrogen gas ($H_2$). Also disclosed are catalyst compositions, for example, that can be used in the dehydrogenation reaction, and methods of preparing such compositions. As a non-toxic, earth-abundant and low-cost oxide material, $ZrO_2$ (e.g., having a small crystallite size of less than about 10 nm, or less than about 20 nm, or less than about 30 nm, or less than about 50 nm, or less than about 1 μm) exhibits a high dehydrogenation rate ($r_d$) during propane dehydrogenation reactions. Pre-treating a standard $ZrO_2$ catalyst (e.g., precipitated using methods known to those of ordinary skill in the art) with carbon monoxide (CO) (e.g., for 30 min at 823 K) prior to use in a dehydrogenation reaction can result in a propane dehydrogenation rate of about 84 mol $kg^{-1}$ $h^{-1}$, which is comparable to dehydrogenation rates exhibited with Pt-based materials. Without being bound to any particular theory, it may be that coordinatively unsaturated Zr sites ($Zr_{cus}$) are the active structures in $ZrO_2$ catalysts. With only a light alkane gas, such as propane ($C_3H_8$), in the inlet stream to a dehydrogenation process, the $ZrO_2$ catalyst may exhibit a half-life of only, for example, 0.2 h at 873 K, and rapid deactivation attributable to the formation of carbonaceous species on the surface of the $ZrO_2$. Regeneration of the $ZrO_2$ catalyst may require frequent cyclic operations based on dehydrogenation reactions and subsequent re-oxidation processes (e.g., in the operation of cycle Catofin-type processes). That is, while $ZrO_2$ catalysts exhibit favorable dehydrogenation activity during dehydrogenation reactions, they can suffer from rapid deactivation due to coke formation.

During investigations of light alkane gas dehydrogenation activity over a catalyst composition comprising $ZrO_2$ according to embodiments, it has been found that by co-feeding $H_2$ with the light alkane gas during the dehydrogenation reaction, the stability of the catalyst can be significantly increased. As set forth in the examples below, further studies have been conducted to verify this observation and to demonstrate the specific effect of $H_2$ on the activity of the catalyst composition comprising $ZrO_2$ during a light alkane dehydrogenation reaction while the bulk crystallite structure of the catalyst composition has been preserved during the reaction. According to various embodiments, the purposeful addition of $H_2$ to light alkane reactants during dehydrogenation reactions on catalyst compositions comprising $ZrO_2$ as the active material, leads to significant stability improvements, with half-life improvements of 100-fold upon addition of the $H_2$. Adding or co-feeding the $H_2$ with the light alkane gas can include introducing the $H_2$ at a pressure of about 1 kPa to about 100 kPa, or at a molar ratio of $H_2$ to light alkane gas of about 1:100 to about 1:1. In embodiments, the $H_2$ and/or reactor can be at a reaction temperature of about 500 K to about 1000 K, or about 873 K. The increase in stability may be attributed to the influence of $H_2$ on the formation of carbonaceous species.

To stabilize the catalyst composition comprising $ZrO_2$, hydrogen ($H_2$) (e.g., about 2-20 kPa) can be co-fed with the light alkane gas (and/or light alkene gas) during the dehydrogenation reaction. A significant increase in the stability of the catalyst composition comprising $ZrO_2$ can be achieved with more than a 100-fold increase in the catalyst's half-life. Without being bound by any particular theory, this increase in stability may be attributable to two factors: 1) the continuous regeneration of Zr active sites; and 2) the inhibition of coke formation via hydrogenative removal. As discussed above, the activity of catalyst compositions comprising $ZrO_2$ may be attributable to Zr surface-active sites on which light alkane molecules can be activated and dehydrogenated to alkenes or which could lead to the formation or organic species that themselves can act as a reaction-derived catalytic function on zirconia surfaces. A higher initial dehydrogenation rate also can be achieved through a pretreatment with a reducing gas (e.g., $H_2$, CO, $NH_3$, etc.) at a corresponding reaction temperature, possibly suggesting the generation of Zr surface-active sites as a result of the reductive pre-treatment. By co-feeding $H_2$ with the light alkane gas (and/or light alkene gas) during the dehydrogenation reaction, it may be that the Zr surface-active sites are continuously regenerated so that loss of active sites due to coke formation are compensated for accordingly.

An inhibition effect on coke formation may be achieved by co-feeding $H_2$ with the light alkane gas (and/or light alkene gas) during dehydrogenation. Quantification of carbon dioxide ($CO_2$) generated during a reoxidation process demonstrates an 80% decrease in total coke amount during a propane dehydrogenation reaction in the presence of $H_2$ as will be discussed in more detail below with respect to FIG. 5. Co-feeding $H_2$ with the light alkane gas (and/or light alkene gas) can maintain and/or increase the number of active sites in a catalyst composition comprising $ZrO_2$ and while simultaneously inhibiting coke formation, resulting in improved stability of catalyst compositions for light alkane gas (and/or light alkene gas) dehydrogenation reactions.

Without being bound by any particular theory, the continuous generation of Zr surface-active sites (e.g., $Zr_{cus}$) may be achieved as the $H_2$ removes lattice oxygen from the surface of the catalyst composition comprising $ZrO_2$. As discussed above, pretreating the catalyst compositions using a reducing gas (e.g., $H_2$, CO, $NH_3$, etc.) is believed to generate Zr surface-active sites and can result in a higher initial dehydrogenation rate ($r_d$). Nonetheless, it has been observed that a continuous decrease in dehydrogenation rate may still exist on reduced catalyst compositions comprising $ZrO_2$ during the dehydrogenation reaction without the presence of additional $H_2$ due to the formation of carbonaceous species. The formation of carbonaceous species on the catalyst surface under reaction conditions has been identified as a main cause of deactivation for most all dehydrogenation catalysts. These carbonaceous species can include hydrogen-poor organic residues that block active sites by hindering contact with reactants and removal of products. Without being bound by any particular theory, it may be that the addition of $H_2$ during the dehydrogenation reaction generates Zr active sites (e.g., $Zr_{cus}$ active sites) by removing surface lattice oxygen, such that the lost active sites covered by carbonaceous species may be compensated during the dehydrogenation reaction; when all of the surface lattice oxygen is removed, this mechanism may change. In embodiments, the $H_2$ can be present in an amount sufficient to remove surface lattice oxygen from the catalyst composition and to generate and/or reactivate surface-active sites. For example, the $H_2$ can be present in an amount of $H_2$ per mass of catalyst of about 1 mol kg$^{-1}$ h$^{-1}$ to about 100 mol kg$^{-1}$ h$^{-1}$, or about 55 mol kg$^{-1}$ h$^{-1}$.

When comparing the amount of carbon dioxide ($CO_2$) generated during the re-oxidation process, a decrease (e.g., 80%) in the amount of carbonaceous species can be observed when $H_2$ (e.g., 12.3 kPa) is added to the light alkane inlet stream at, for example, a temperature of about 873 K. The decrease in the amount of carbonaceous species formed can be attributable to the inhibited adsorption of certain polymerization intermediates (e.g., $C_2H_4$, $C_3H_6$, etc.) as the catalyst surface is populated and present in equilibrium with the added $H_2$.

Catalyst Compositions

Catalyst compositions as described herein are useful in dehydrogenation reactions, for example, to dehydrogenate light alkane gases to form alkenes. In embodiments, the catalyst compositions can also be used to dehydrogenate light alkene gases to form alkadienes. According to embodiments, the catalyst compositions can comprise $ZrO_2$. The $ZrO_2$ is the active catalyst material in the dehydrogenation reactions according to various embodiments disclosed herein. In embodiments, the $ZrO_2$ is not inactive or an inactive support, rather it is the active catalyst material.

As will be discussed in more detail below, the catalyst composition may comprise an additive, such as yttrium, to increase the sintering stability and thus preserve the tetragonal phase of $ZrO_2$. The catalyst composition may also be free of at least one of chromium and a precious metal. Non-limiting examples of precious metals include platinum (Pt), gold (Au), silver (Ag), copper (Cu), palladium (Pd) and combinations thereof. In embodiments, the catalyst composition is free of both chromium and platinum. Catalyst compositions as described herein may present fewer risks to human health and the environment than other known catalysts, e.g., chromium- and platinum-based catalysts, used for dehydrogenation.

In embodiments, the catalyst composition can include at least about 50 wt % $ZrO_2$, at least about 60 wt % $ZrO_2$, at least about 70 wt % $ZrO_2$, at least about 80 wt % $ZrO_2$, at least about 90 wt % $ZrO_2$, or about 85 wt % $ZrO_2$, about 90 wt % $ZrO_2$, about 95 wt % $ZrO_2$, about 96 wt % $ZrO_2$, about 97 wt % $ZrO_2$, about 98 wt % $ZrO_2$, about 99 wt % $ZrO_2$, about 99.5 wt % $ZrO_2$, or about 100 wt % $ZrO_2$. In embodiments, the catalyst composition can include about 50 wt % to about 100 wt % $ZrO_2$, or about 60 wt % to about 100 wt % $ZrO_2$, or about 70 wt % to about 100 wt % $ZrO_2$, about 80 wt % to about 100 wt % $ZrO_2$, or about 90 wt % to about 100 wt % $ZrO_2$.

Catalyst compositions according to embodiments herein can contain a plurality of surface-active sites. Without being bound by any particular theory, for catalyst compositions comprising $ZrO_2$, it may be that the surface-active sites are coordinatively unsaturated Zr sites ($Zr_{cus}$). According to embodiments, catalyst compositions comprising $ZrO_2$ comprise a plurality of $Zr_{cus}$ surface-active sites.

The catalyst compositions can be measured by X-ray diffraction (XRD), e.g., using a Siemens D5000 unit at ambient temperature with Cu Kα radiation and a scan rate of 0.033° s$^{-1}$ to determine the crystalline structure of the catalyst composition. Catalyst compositions comprising $ZrO_2$ in embodiments disclosed herein can be in at least one of the monoclinic phase and the tetragonal phase, for example, as measured by XRD as described in Zhang, et al., *The Effect of Phase Composition and Crystallite Size on Activity and Selectivity of $ZrO_2$ in Non-Oxidative Propane Dehydrogenation*, J. of Catalysis, 371, 313-324 (2019), which is incorporated herein by reference in its entirety. In embodiments, the catalyst composition comprises $ZrO_2$ in the monoclinic phase.

The Brunauer, Emmett and Teller (BET) surface area of the catalyst composition can be measured using nitrogen ($N_2$) physisorption uptake at its normal boiling point in a surface analyzer (e.g., a Quantasorb® 6 Surface Analyzer by Quantachrome® Corp.). The BET surface area can be measured as set forth in Otroshchenko, et al., *$Zr_2$-Based Unconventional Catalysts for Non-Oxidative Propane Dehydrogenation: Factors Determining Catalytic Activity*, J. of Catalysis, 348, 282-290 (2017), which is incorporated herein by reference in its entirety. Another suitable method of measuring the BET surface area is set forth in ASTM D3663-03(2008), which is incorporated by reference herein in its entirety. Catalyst compositions comprising $ZrO_2$ as described herein can have a BET surface area of about 1 m$^2$ g$^{-1}$ to about 100 m$^2$ g$^{-1}$, or about 10 m$^2$ g$^{-1}$ to about 90 m$^2$ g$^{-1}$, or about 20 m$^2$ g$^{-1}$ to about 80 m$^2$ g$^{-1}$, 30 m$^2$ g$^{-1}$ to about 70 m$^2$ g$^{-1}$, 40 m$^2$ g$^{-1}$ to about 60 m$^2$ g$^{-1}$, or about 40 m$^2$ g$^{-1}$, or about 45 m$^2$ g$^{-1}$, or about 50 m$^2$ g$^{-1}$ as measured by a surface analyzer as described above.

According to various embodiments, the catalyst composition comprising $ZrO_2$ can further include a rare earth metal. In embodiments, the rare earth metal can include at least one lanthanide metal, an oxide thereof and combinations thereof. According to embodiments, the rare earth metal can be at least one of yttrium (Y), erbium (Er), cerium (Ce), dysprosium (Dy), gadolinium (Gd), lanthanum (La), neodymium (Nd), samarium (Sm), ytterbium (Yb), oxides thereof and mixtures thereof. In embodiments, the catalyst composition can include about 0.5 wt % to about 50 wt %, or about 1 wt % to about 40 wt %, or about 2 wt % to about 30 wt %, or about 3 wt % to about 25 wt %, or about 4 wt % to about 20 wt %, or about 5 wt % to about 15 wt %, or about 1 wt % to about 12 wt %, or about 2 wt % to about 10 wt % of the rare earth metal, an oxide thereof or mixtures thereof. In certain embodiments, the catalyst composition can include $ZrO_2$ stabilized with an yttrium dopant. The yttrium can increase the surface area of $ZrO_2$ and stabilizes the pure tetragonal phase of the $ZrO_2$. Such catalyst compositions can comprise about 85 wt % to about 99.5 wt % $ZrO_2$ and about 0.5 wt % to about 15 wt % $Y_2O_3$ and/or anatomic ratio of Y/Zr of greater than 0 to about 0.2. The catalyst composition comprising the yttria-stabilized zirconia (YSZ) can have a BET surface area of about 40 $m^2 g^{-1}$ to about 110 $m^2 g^{-1}$.

According to various embodiments, a catalyst composition comprising $ZrO_2$ can be treated with a pretreatment gas. Pretreating the catalyst composition can increase the number of surface-active sites on the catalyst, which can result in higher catalytic activity during the dehydrogenation reaction (e.g., at the beginning of the reaction). For example, without being bound by any particular theory, it may be that pretreating a catalyst composition comprising $ZrO_2$ can increase the Zr surface-active sites as compared to a catalyst composition that has not been pretreated. In embodiments, a pretreated catalyst composition containing $ZrO_2$ comprises more surface-active sites (e.g., $Zr_{cus}$) than a catalyst composition containing $ZrO_2$ that has not been pretreated.

In embodiments, a pretreated catalyst composition can be formed by contacting the catalyst composition with a pretreatment gas under certain conditions. The pretreatment gas can include a reducing agent comprising at least one of $H_2$, carbon monoxide (CO), ammonia and methane ($CH_4$). In embodiments, the pretreatment gas can further include an inert gas comprising at least one of nitrogen ($N_2$), helium (He) and Argon (Ar). In embodiments, the pretreatment gas can comprise the reducing agent at a concentration of about 1 mol % to about 10 mol %, or about 2 mol %, or about 4 mol %, or about 6 mol %, or about 8 mol %, or about 10 mol %. In certain embodiments, the pretreatment gas is $H_2$ and can include about 1 mol % to about 10 mol % $H_2$, or about 2 mol % $H_2$, or about 4 mol % $H_2$, or about 6 mol % $H_2$, or about 8 mol % $H_2$, or about 10 mol % $H_2$.

During the pretreatment, the pretreatment gas and/or the catalyst composition can be at a temperature of at least about 850 K, or at least about 860 K, or at least about 870 K, or at least about 873 K, or at least about 880 K, or at about 870 K, or at about 871 K, or at about 872 K, or at about 873 K, or at about 874 K, or at about 875 K. The pretreatment gas can be in contact with the catalyst composition for about 1 h to about 24 h, or about 2 h to about 22 h, or about 3 h to about 20 h, or about 5 h to about 15 h, or about 8 h to about 12 h, or about 1 h, or about 2 h, or about 3 h, or about 4, hour or about 5 h.

According to various embodiments, catalyst compositions as disclosed herein can be in the form of a plurality of units. The plurality of units can include, but are not limited to, particles, powder, extrudates, tablets, pellets, agglomerates, granules and combinations thereof. The plurality of units can have any suitable shape known to those of ordinary skill in the art. Non-limiting examples of shapes include round, spherical, spheres, ellipsoidal, cylinders, hollow cylinders, four-hole cylinders, wagon wheels, regular granules, irregular granules, multilobes, trilobes, quadrilobes, rings, monoliths and combinations thereof.

The plurality of units can be formed by any suitable method known to those of ordinary skill in the art. Non-limiting examples of methods for shaping and forming a plurality of units (e.g., from a mixture of catalyst materials) include, extrusion, spray drying, pelletization, agglomeration, oil drop, and combinations thereof. In one embodiment, the plurality of units can be formed by pressing a powder into wafers (e.g., at about 690 bar, for about 0.05 h), crushing the wafers and then sieving the resulting aggregates to retain a mean aggregate size of about 100 µm to about 250 µm, or about 1.5 mm to about 5 mm, or about 80 mesh to about 140 mesh.

In certain embodiments, the plurality of units can have a size of less than about 1,000 µm, or less than about 750 µm, or less than about 500 µm, or less than about 300 µm, or less than about 250 µm, or less than about 225 µm, or less than about 200 µm, or less than about 190 µm, or less than about 180 µm, or less than about 150 µm, or less than about 100 µm, or less than about 10 µm as measured by any suitable method known to those of ordinary skill in the art. In embodiments, the plurality of units can have a size of about 170 µm to about 250 µm, or about 80 mesh to about 140 mesh. In further embodiments, the plurality of units have a mean size of about 1.5 mm to about 15.0 mm, or about 1.5 mm to about 12 mm, or about 1.5 mm to about 10 mm, or about 1.5 mm to about 8.0 mm, or about 1.5 mm to about 5.0 mm. Particle size can be measured using any suitable method known to those of ordinary skill in the art. For example, particle size can be measured using ASTM D4438-85(2007) and ASTM D4464-10, both of which are incorporated herein by reference in their entirety.

According to embodiments, catalyst compositions as described herein may be comprised in a kit. The kit can include the catalyst composition as described above and instructions for pretreating the catalyst composition. The instructions can comprise the following elements: 1) place the catalyst composition in a chamber and/or reactor; 2) heat the pretreatment gas, the chamber, the reactor and/or the catalyst composition to a temperature of at least about 850 K, or at least about 860 K, or at least about 870 K, or at least about 873 K, or at least about 880 K. or at about 870 K, or at about 871 K, or at about 872 K, or at about 873 K, or at about 874 K, or at about 875 K; 3) introduce the pretreatment gas into the chamber and/or reactor and contact the catalyst composition with the pretreatment gas for about 0.1 h to about 24 h, or about 0.5 h to about 22 h, or about 1.0 h to about 20 h, or about 2.5 h to about 15 h, or about 5 h to about 12 h, or about 0.1 h, or about 0.2 h, or about 0.5 h, about 1 h, or about 2 h, or about 3 h, or about 4, hour or about 5 h.

According to embodiments, the kit may include the catalyst composition together with instructions for using the catalyst composition in a light alkane (or light alkene) dehydrogenation process. The catalyst composition can be pretreated or may not be pretreated in accordance with embodiments herein. If not pretreated, the kit can further include instructions for pretreating the catalyst composition as described above. The instructions for using the catalyst composition can comprise the following elements: 1) place the catalyst composition in a reactor; 2) introduce the light alkane gas (and/or light alkene gas) together with $H_2$ into the reactor; and 3) contact the light alkane gas (and/or light alkene gas) and the $H_2$ with the catalyst composition. Optionally, the instructions may further include 4) recover the dehydrogenated (i.e., alkene or alkadiene) gas.

The kits discussed above can include suitable details and instructions for using the catalyst composition safely and productively. Non-limiting examples of such details and instructions can include how to load the catalyst composition into the reactor, how to pre-treat the catalyst composition, if necessary, before starting the reaction, the starting temperatures and gas composition for bringing the catalyst composition on-stream, the regeneration procedures, how to unload the catalyst composition from the reactor and combinations thereof.

Methods of Preparing the Catalyst Compositions

According to various embodiments, disclosed herein are methods of preparing catalyst compositions as described above. A catalyst composition comprising $ZrO_2$ can be prepared using a hydrothermal approach. In embodiments, the catalyst composition comprising $ZrO_2$ can be synthesized by dissolving an amount of $ZrO(NO_3)_2 \cdot xH_2O$ in an amount of water (e.g., deionized water) at a weight ratio of water to $ZrO(NO_3)_2 \cdot xH_2O$ of about 1:1 to about 5:1, or about 2:1 to about 4:1, or about 2:1, or about 2.3:1, or about 2.4:1, or about 3:1, or about 4:1. Separately urea can be dissolved in water at a weight ratio of water to urea of about 1:2 to about 4:1, or about 1:1 to about 3:1, or about 1.5:1 to about 2:1, or about 1.1:1, or about 1.2:1, or about 1.3:1, or about 1.4:1. The $ZrO(NO_3)_2 \cdot xH_2O$ and urea solutions can be mixed together at a temperature of about 20° C. to about 25° C. and then transferred to an autoclave formed of a suitable material (e.g., stainless steel or other metallurgy, Teflon® or other suitable polymer). The mixture can be crystallized in the autoclave at an elevated temperature, for example, a temperature of about 300 K to about 500 K, or about 320 K to about 480 K, or about 350 K to about 460 K, or about 400 K, or about 450 K, or about 451 K, or about 452 K, or about 453 K, or about 454 K, or about 455 K under autogenous pressure for a period of time, for example, about 2 h to about 36 h, or about 5 h to about 32 h, or about 10 h to about 24 h, or about 12 h to about 20 h, or about 18 h, or about 19 h, or about 20 h, or about 21 h, or about 22 h. The crystalline precipitate can be washed with deionized water, for example, at a ratio of about 50 mL to about 250 mL of deionized water per gram of catalyst, or about 100 mL deionized water per g catalyst and subsequently dried under air at a temperature of about 300 K to about 500 K, or about 325 K to about 450 K, or about 350 K to about 400 K, or about 380 K, or about 381 K, or about 382 K, or about 383 K, or about 384 K, or about 385 K, for a period of about 6 h to about 24 h, or about 8 h to about 22 h, or about 10 h to about 20 h, or about 12 h to about 18 h. In embodiments, the crystalline precipitate can be calcined according to any suitable method known to those of ordinary skill in the art. For example, the crystalline precipitate can be calcined in flowing dry air (e.g., zero grade) at a flow rate of about 0.5 $cm^3$ $s^{-1}$ to about 2.00 $cm^3$ $s^{-1}$, or about 1.67 $cm^3$ $s^{-1}$ and a temperature of about 700 K to about 1,000 K, or about 750 K to about 950 K, or about 800 K to about 900 K, or about 870 K, or about 871 K, or about 872 K, or about 873 K, or about 874 K, or about 875 K, or about 923 K, for about 1 h to about 6 h, or about 3 h.

In embodiments, a catalyst composition comprising yttrium stabilized zirconium oxide can be prepared. The catalyst composition can be synthesized by combining $ZrO(NO_3)_2$ with $Y(NO_3)_3$, $NH_4OH$ and $H_2O$ to form a mixture. The mixture can be transferred to an autoclave to be crystallized at an elevated temperature of about 250 K to about 500 K, or about 275 K to about 480 K, or about 290 K to about 460 K, or about 295 K, or about 296 K, or about 297 K, or about 298 K, or about 299 K, or about 300 K, or about 301 K under autogenous pressure for a period of time, for example, about 2 h to about 36 h, or about 5 h to about 32 h, or about 10 h to about 24 h, or about 12 h to about 20 h, or about 10 h, or about 11 h, or about 12 h, or about 13 h, or about 14 h. The crystalline precipitate can be washed with deionized water, for example, at a ratio of about 50 mL to about 250 mL of deionized water per gram of catalyst, or about 100 mL deionized water per g catalyst, and subsequently dried under air at a temperature of about 300 K to about 500 K. or about 325 K to about 450 K, or about 350 K to about 400 K, or about 380 K, or about 381 K, or about 382 K. or about 383 K, or about 384 K, or about 385 K, for a period of about 6 h to about 24 h, or about 8 h to about 22 h, or about 10 h to about 20 h, or about 12 h to about 18 h. In embodiments, the crystalline precipitate can be calcined according to any suitable method known to those of ordinary skill in the art. For example, the crystalline precipitate can be calcined in flowing dry air (e.g., zero grade) at a flow rate of about 0.5 $cm^3$ $s^{-1}$ to about 2.00 $cm^3$ $s^{-1}$, or about 1.67 $cm^3$ $s^{-1}$ and a temperature of about 700 K to about 1.000 K, or about 750 K to about 950 K, or about 800 K to about 900 K, or about 870 K, or about 871 K, or about 872 K, or about 873 K, or about 874 K, or about 875 K, or about 923 K, for about 1 h to about 6 h, or about 3 h.

According to embodiments, methods of preparing the catalyst composition can further include pretreating the catalyst composition in a pretreatment gas as discussed above. For example, the catalyst composition can be subjected to a reductive pretreatment, for example, with a pretreatment gas comprising at least one of $H_2$, carbon monoxide (CO), light alkanes, propane ($C_3H_8$), alkenes, propene ($C_3H_6$) and $H_2$ species present as reactant and products of the dehydrogenation reaction. In embodiments, the catalyst composition can be pretreated with $H_2$ at a temperature of about 800 K to about 1,000 K, or about 850 K to about 900 K, or about 873 K. The pretreated catalyst composition can include more surface-active sites (e.g., $Zr_{cus}$ surface-active sites) than a catalyst composition that has not been pretreated.

Methods of Using the Catalyst Compositions

Further described are methods of using catalyst compositions according to embodiments. In embodiments, the catalyst compositions can be used in the dehydrogenation of light alkane gas to form alkenes. In embodiments, the methods can also be used in the dehydrogenation of light alkene gas to form alkadienes. The $ZrO_2$ present in the catalyst compositions is the active catalyst material in the dehydrogenation reactions as disclosed herein. In contrast to, e.g., the Oleflex® process where $ZrO_2$ is used as an inactive support for the active Pt—Sn catalyst materials, the $ZrO_2$ in the present catalyst compositions is the active catalyst material. It is believed that $ZrO_2$ has not before been used as the active catalyst material for the dehydrogenation of light alkane (and/or light alkene) gas according to embodiments herein.

In embodiments, when preparing to dehydrogenate a light alkane gas, the catalyst composition (e.g., at a weight hourly space velocity of about 5.5 $h^{-1}$ to about 0.05 $h^{-1}$, or about 5.4 $h^{-1}$ to about 0.054 $h^{-1}$, or about 2.7 $h^{-1}$ to about 1.8 $h^{-1}$, or about 5.0 $h^{-1}$ to about 0.1 $h^{-1}$) can be placed within a reactor and held at an about constant temperature using a furnace and a temperature controller (e.g., a Watlow Series 96). The reactor can be any suitable reactor known to those of ordinary skill in the art. Non-limiting examples include a U-shape quartz reactor (e.g., with an inner diameter of about 11.0 mm), a packed tubular reactor, a catofin-type reactor, a fluidized bed reactor, a fixed bed reactor and a moving bed reactor. The furnace may be any suitable furnace known to those of ordinary skill in the art. Non-limiting examples include a single zone furnace (e.g., by National Element Inc., Model No. BA-120), a batchwise furnace or a quartz tube furnace.

Prior to dehydrogenation, the catalyst composition can be treated in a flowing oxygen gas ($O_2$) and helium (He) mixture at a molar ratio of 02 of 20:1 to about 30:1, or about 22:1 to about 28:1, or about 24:1 and heating the flowing gas mixture to a temperature of about 800 K to about 1,000 K, or about 850 K to about 900 K, or about 873 K at a rate of about 0.1 K s' to about 1 K $s^{-1}$, or about 0.167 K $s^{-1}$. Treating the catalyst composition with the flowing $O_2$ and He gas mixture can be for a period of about 0.5 h to about 8 h, or about 1 h to about 4 h, or about 1 h, or about 2 h. Subsequently, the reactor can be purged with flowing inert gas (as defined above), steam, or by vacuum (e.g., 2 $cm^3$ $g^{-1}$ $s^{-1}$, ultra-high purity) to remove residual $O_2$ within the reactor.

The light alkane gas (and/or light alkene gas) can be introduced to the reactor in the presence of the catalyst composition. According to embodiments, the light alkane gas (and/or light alkene gas) can comprise any one of a $C_2$ to $C_5$ straight or branched alkane and mixtures thereof. In embodiments, the light alkane gas (and/or light alkene gas) can comprise at least one of ethane, propane, n-butane, isobutane, pentane and mixtures thereof. In embodiments, a portion of the effluent from the reactor can be recycled to the gas inlet and combined with fresh feed gas. The effluent can comprise alkenes, for example, at least one of ethene, pentene, butene, isobutene and pentene, and unreacted light alkanes comprising at least one of ethane, propane, n-butane, isobutane and pentane. In embodiments, the light alkane gas (and/or light alkene gas) can be mixed with an inert gas (e.g., steam, He, $N_2$, Ar) at a molar ratio of about 1:2 to about 2:1, or about 1:1. In embodiments, a vacuum pump can be used to lower the pressure of the reactants while maintaining the total pressure above, for example, 1 bar to allow convective flow when the exit pressure is atmospheric.

Methods of dehydrogenating light alkane gas (and/or light alkene gas) can include co-feeding $H_2$ with the light alkane gas (and/or light alkene gas) in the presence of the catalyst composition. The catalyst composition can comprise $ZrO_2$ according to various embodiments described herein. Adding or co-feeding the $H_2$ with the light alkane gas (and/or light alkene gas) can include introducing the $H_2$ at a pressure of about 1 kPa to about 100 kPa, or about 5 kPa to about 75 kPa, or about 10 kPa to about 50 kPa, or about 30 kPa to about 50 kPa while dehydrogenating the light alkane gas. In embodiments, the $H_2$ can be added to the light alkane gas (and/or light alkene gas) at a molar ratio of $H_2$ to light alkane gas (and/or light alkene gas) of about 1:100 to about 1:1. In embodiments, the $H_2$ and/or reactor can be at a temperature of about 500 K to about 1000 K, or about 550 K to about 950 K, or about 600 K to about 900 K, or about 700 K to about 900 K.

According to embodiments, the method of dehydrogenating a light alkane gas (and/or light alkene gas) in the presence of $H_2$ and a catalyst composition as described herein can provide a dehydrogenation rate per mass of the catalyst composition of about 0.5 mol $kg^{-1}$ $h^{-1}$ to about 10.0 mol $kg^{-1}$ $h^{-1}$, or about 0.6 mol $kg^{-1}$ $h^{-1}$ to about 8.3 mol $kg^{-1}$ $h^{-1}$. The light alkane gas (and/or light alkene gas) dehydrogenation rate and cracking rate can be determined by analyzing the effluent stream from the reactor using gas chromatography (e.g., by an Agilent® 1540A gas chromatograph) with flame ionization detection (FID) (e.g., a GC fitted with a GS-GASPRO column) after chromatographic separation. In embodiments, the light alkane gas (and/or light alkene gas) dehydrogenation rate and the cracking rate can be normalized by the mass of the catalyst composition (e.g., in mol $kg^{-1}$ $h^{-1}$). In embodiments, the light alkane gas (and/or light alkene gas) dehydrogenation rate and cracking rate can be determined at a temperature of 873 K and 823 K. The temperature can be measured using any suitable method known to those of ordinary skill in the art. In embodiments, the temperature can be measured with a thermocouple (e.g., a K-type thermocouple by Omega®) and the reactor temperature can be determined from a thermocouple placed in contact with an outer tube surface (e.g., made of metal, quartz, etc.) at the catalyst bed midpoint.

In embodiments, when used in a dehydrogenation reaction as described above, catalyst compositions as disclosed herein can provide improved stability over other known catalyst compositions for the dehydrogenation of light alkanes (and/or light alkenes). The half-life of the catalyst composition in the dehydrogenation reaction can be measured using any suitable method known to those of ordinary skill in the art. In embodiments, the term "half-life of the catalyst composition" can refer to the number of days or hours after which the catalyst device has a dehydrogenation rate (DR) that is 50% lower than an initial or maximum dehydrogenation rate ($DR_i$) value produced by the catalyst composition at the start (or soon after the start upon stabilization) of the catalyst composition's operation (e.g., the half-life of the catalyst composition can be based on the dehydrogenation reaction rate as a function of time). In embodiments, the half-life of the catalyst composition is related to the weight hourly space velocity (WHSV), which is the hourly mass feed flow rate per catalyst mass ($h^{-1}$) in the reactor. In embodiments, the catalyst composition can have a half-life of about 1 h to about 50 h, or about 6 h to about 46 h when the WHSV is about 5.4 $h^{-1}$ to about 0.054 $h^{-1}$.

The half-life of the catalyst composition can also be evaluated when aging the composition under different conditions. The DR can be calculated based on Formula I:

$$DR=60 \cdot (k_e-k_n) \cdot V \quad \quad \text{Formula I}$$

wherein $k_e$ represents the total decay constant, k represents natural decay constant, V represents the chamber volume in $m^3$, and ($k_e-k_n$) is calculated based on Formula II:

$$(k_e-k_n) \cdot t = -\ln(C_t/C_0) \quad \quad \text{Formula II}$$

wherein t represents the total testing time, $C_t$ represents the concentration at time t in mg/$m^3$, and $C_0$ represents the concentration at time t=0 in mg/$m^3$.

To determine the half-life of the catalyst composition, testing can begin by obtaining the DR value produced by the catalyst composition at the start of the catalyst composition's operation or soon after the start of the catalyst composition's operation once the DR has stabilized (t=0), also known as $DR_0$. Subsequently, the catalyst composition can be optionally subjected to an Acceleration Test. An "Acceleration Test" refers to an extreme condition that may impact or deteriorate the efficacy of the catalyst composition more rapidly, such as no $H_2$ gas co-feed or pre-treatment, co-feeding with $O_2$, introducing a pollutant or continuous generation of pollutants. The optional Acceleration Test results can allow the estimation of the catalyst composition's life span under real-life conditions. Following the optional Acceleration Test, the catalyst composition is then aged under real-life conditions.

After the catalyst composition is aged for eight hours under real-life conditions, another sample is taken to obtain the $DR_n$ value at t=n, also known as $DR_n$. If the $DR_n$ value is greater than 50 percent of the $DR_n$ value, then the catalyst composition is considered as still operable and the testing continues by repeating the optional acceleration test, aging the catalyst device under real-life conditions, and measuring the $DR_n$ value after each subsequent cycle. Once the $DR_n$ value is lower or equal to 50 percent of the $DR_0$ value, the life span of the catalyst device is deemed to have ended and the overall alkene mass (AM) generated by the catalyst composition is calculated.

The above-described methods of using the catalyst compositions to dehydrogenate light alkane gas, can also be used to dehydrogenate a light alkene gas to form alkadienes. A light alkene gas can include $C_2$-$C_5$ branched or straight alkenes. In embodiments, two reactors can be configured in series, the first for dehydrogenating light alkane gas and the second for dehydrogenating the light alkene gas.

EXAMPLES

Example 1—Crystal Structure of $ZrO_2$

A $ZrO_2$ catalyst composition was prepared using a hydrothermal approach. To synthesize the $ZrO_2$, 12.7 g $ZrO(NO_3)$ $2xH_2O$ (99%, Aldrich) were dissolved in 30 mL deionized $H_2O$ and 21.6 g urea were dissolved in 30 mL deionized $H_2O$ separately. The resulting solutions were mixed together at room temperature and then transferred into a Teflon lined stainless-steel autoclave. Crystallization was performed at 453 K under autogenous pressure for 20 h. After completion of the crystallization process, the precipitate was washed thoroughly with 500 ml deionized water and then dried under air at 383 K overnight.

The crystal structure of the resulting $ZrO_2$ catalyst composition was measured using X-ray diffraction. The XRD pattern of $ZrO_2$ catalyst composition is shown in FIG. 1. The data herein indicates that catalyst compositions as described can retain the tetragonal phase at all temperatures of treatment while providing higher dehydrogenation rates.

Example 2—Effect of Pretreatment on Initial $C_3H_8$ Dehydrogenation Rate ($r_d$) at 873 K The effect of pretreating the $ZrO_2$ catalyst composition as prepared in Example 1 on initial propane dehydrogenation (PDH) rate ($r_d$) at 873 K was evaluated. In order to compare the effect of oxidative and reductive pretreatments on PDH activity of the $ZrO_2$ catalyst composition, the catalyst was pretreated in a 4 mol % $O_2$/He mixture at 873 K for 2 h and separately in a 10 mol % $H_2$/He mixture at 873 K for 2 h prior to the PDH reaction.

Figure 2A:
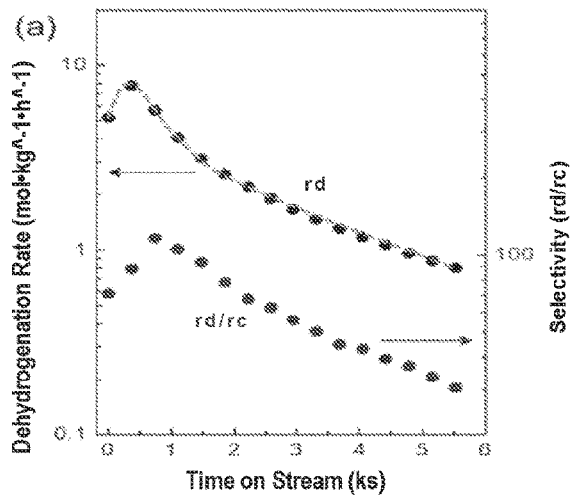
FIG. 2a shows the dehydrogenation rate per mass of catalyst ($r_d$) and the selectivity of the dehydrogenation reaction (ratio between dehydrogenation and cracking rate, $r_d/r_c$) during a propane dehydrogenation (PDH) reaction on a pretreated $ZrO_2$ catalyst.

The $O_2$/He pretreated $ZrO_2$ catalyst was introduced into the reactor. During the propane dehydrogenation reaction, the propane feed gas was at a pressure of 13.7 kPa and a temperature of 873 K and the catalyst composition was at a temperature of 873 K. As shown in FIG. 2A, an initial increase in dehydrogenation rate (per mass) was observed within 6 min of the reaction. The dehydrogenation rate increased from 5.2 mol kg$^{-1}$ h$^{-1}$ to 7.8 mol kg$^{-1}$ h$^{-1}$ while the selectivity of the PDH reaction (ratio between dehydrogenation and cracking rate ($r_d/r_c$)) also increased from 71 to 88 during this 6 min activation period. A monotonic decrease in dehydrogenation rate and selectivity was observed after the initial activation period indicating the deactivation of $ZrO_2$ catalyst. Without being bound by any particular theory, the increase in dehydrogenation rate during the initial activation period may indicate the presence of an activation effect. Because the surface lattice oxygen was removed, Zr surface active sites possibly were generated leading to a higher dehydrogenation rate.

After the initial activation period of 6 min, the dehydrogenation rate and selectivity ($r_d/r_c$) of $ZrO_2$ catalyst decreased with time. The deactivation process follows a first-order deactivation mechanism as shown in equation 1:

$$\ln\left(\frac{r_i}{r_0}\right) = -k_d t \qquad (1)$$

where $r_0$ is the maximum dehydrogenation rate at the beginning of PDH reaction or during the initial activation period, $r_i$ is the dehydrogenation rate at different time on stream and $k_d$ is the deactivation constant. The half-life of the catalyst is defined in equation 2, which is time elapsed as the catalyst deactivates to one-half of its initial dehydrogenation rate:

$$t_{0.5} = \left|\frac{\ln(0.5)}{k_d}\right| \qquad (2)$$

FIG. 2A shows that after the initial activation period during PDH reaction at 873 K, a half-life of 0.28 h can be observed for the $ZrO_2$ catalyst pretreated in $O_2$/He at 873 K and the deactivation is mainly caused by the formation of carbonaceous species on the surface, as the spent catalyst exhibited black color. This observation confirms previous observations (see, e.g., Zhang, et al., *Control of Coordinatively Unsaturated Zr Sites in $ZrO_2$ for Efficient C-H Bond Activation*, Nature Communications, 9 (1), 3794 (2018)) that $ZrO_2$ catalysts during PDH reaction suffer from rapid deactivation with a catalyst's half-life of 0.2 h during PDH reaction at 873 K under 40 kPa $C_3H_8$ and require regeneration on a regular basis.

Figure 2B:
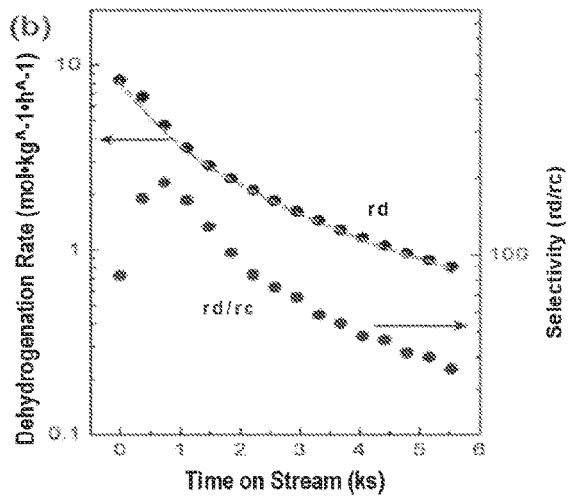
FIG. 2b shows the dehydrogenation rate per mass of catalyst ($r_d$) and selectivity of the dehydrogenation reaction (ratio between dehydrogenation and cracking rate, $r_d/r_c$) during a PDH reaction on a pretreated $ZrO_2$ catalyst.

A fresh catalyst was treated in flowing 10% $H_2$/He mixture at 873 K for 2 h. As shown in FIG. 2B, for the $ZrO_2$ catalyst pretreated in the $H_2$/He, the initial activation period was not observed during the PDH reaction at 873 K. The initial dehydrogenation rate was 8.3 mol kg$^{-1}$ h$^{-1}$, which is comparable to the highest dehydrogenation (i.e., 7.8 mol kg$^{-1}$ h$^{-1}$) during initial activation period on $ZrO_2$ treated in 4% $O_2$/He at 873 K. This indicates that a reductive pretreatment by $H_2$ can activate $ZrO_2$ to a similar extent as an oxidative pretreatment during the initial activation period. The dehydrogenation rate on $ZrO_2$ treated in $H_2$/He at 873 K decreased monotonically with time on stream with a half-life of 0.32 h, a value similar to that on $ZrO_2$ treated in $O_2$/He at 873 K (0.28 h). This indicates that the deactivation behavior is not affected by pretreatment methods (oxidative or reductive). Based on the above observation, it was determined that $H_2$ can activate the $ZrO_2$ catalyst through $H_2$/He pretreatment before the PDH reaction.

Example 3—Dehydrogenation Rate Per Mass of Catalyst ($r_d$) During a $C_3H_8$ Dehydrogenation Reaction on a Pretreated $ZrO_2$ Catalyst The dehydrogenation rate per mass of catalyst ($r_d$) during a PDH reaction on a pretreated $ZrO_2$ catalyst was determined. A ZrO$_2$ catalyst composition as prepared in Example 1 was pretreated with O$_2$ at a pressure of 4 kPa and a temperature of 823 K for 2 h. Separately, another ZrO$_2$ catalyst composition as prepared in Example 1 was pretreated in H$_2$ at a pressure of 10 kPa and a temperature of 873 K for 2 h. The effect of pretreatment was then studied for a PDH reaction at 823 K on the ZrO$_2$ catalyst During the PDH reaction, propane was introduced to the reactor at a pressure of 13.7 kPa and a temperature of 823 K.

Figure 3:
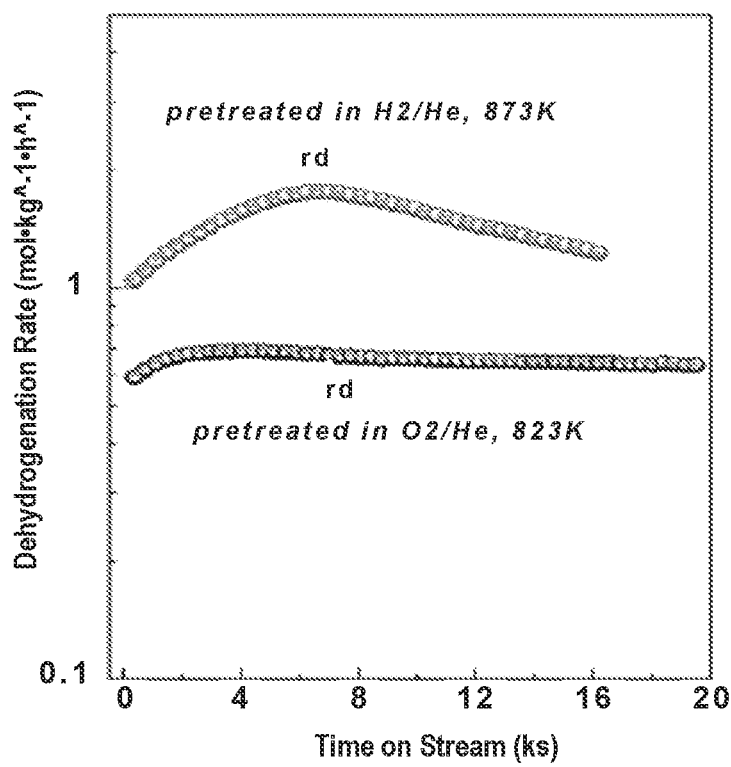
FIG. 3 shows the dehydrogenation rate per mass of catalyst ($r_d$) during a PDH reaction on a pretreated $ZrO_2$ catalyst.

As shown in FIG. 3, after the catalyst was treated in O$_2$/He at 823 K, an initial activation effect was observed, which lasted for 70 min with an increase in dehydrogenation rate from 0.6 mol kg$^{-1}$ h$^{-1}$ to 0.7 mol kg$^{-1}$ h$^{-1}$. After the initial activation period, the catalyst started to deactivate at a much slower rate as compared to the deactivation process during the PDH reaction at 873 K (Example 2). Moreover, for the PDH reaction at 823 K, there is no contribution to cracking rate from the ZrO$_2$ catalyst and all cracking products detected can be attributed to homogenous gas phase reactions of propane, which can occur even in empty reactors at these temperatures. The half-life for the catalyst pretreated with O$_2$/He during PDH reaction at 823 K was 34 h, which is 120 times higher than the half-life during the PDH reaction at 873 K (0.28 h). The ZrO$_2$ catalyst treated in H$_2$/He at 873 K had a higher initial dehydrogenation rate (1.1 mol kg$^{-1}$ h$^{-1}$) compared with the catalyst (0.7 mol kg$^{-1}$ h$^{-1}$) treated in O$_2$/He at 823 K during PDH reaction at 823 K. These data demonstrate the activation effect of the H$_2$ pretreatment (FIG. 3).

Different from the PDH reaction at 873 K on the ZrO$_2$ catalyst treated in H$_2$/He at 873 K where no initial activation period can be observed, the PDH reaction at 823 K on the ZrO$_2$ catalyst treated in H$_2$/He at 873 K exhibited an initial activation period (110 min, up to 1.8 mol kg$^{-1}$ h$^{-1}$). This indicates that the pre-reduced ZrO$_2$ can be further activated during the PDH reaction by propane-derived species. A 6 h half-life can be observed for ZrO$_2$ treated in H$_2$/He at 873 K during PDH reaction at 823 K, as compared to the ZrO$_2$ catalyst treated in O$_2$/He at 823 K (34 h).

Example 4—Effect of Co-Feeding H$_2$ on the Stability of ZrO$_2$ Catalyst at 873 K and 823 K The effect of co-feeding H$_2$ with the light alkane gas (e.g., propane) during a dehydrogenation reaction in the presence of a ZrO$_2$ catalyst (as prepared in Example 1) was evaluated. The dehydrogenation rate per mass ($r_d$) of ZrO$_2$ catalyst pretreated with O$_2$/He, with additional H$_2$ present during the PDH reaction at different temperatures, was determined. During the PDH reaction, H$_2$ was introduced to the reactor at a pressure of 12.3 kPa and C$_3$H$_8$ was co-introduced at a pressure of 13.7 kPa. The reaction was performed at a temperature of 873 K and separately at a temperature 823 K.

Figure 4:
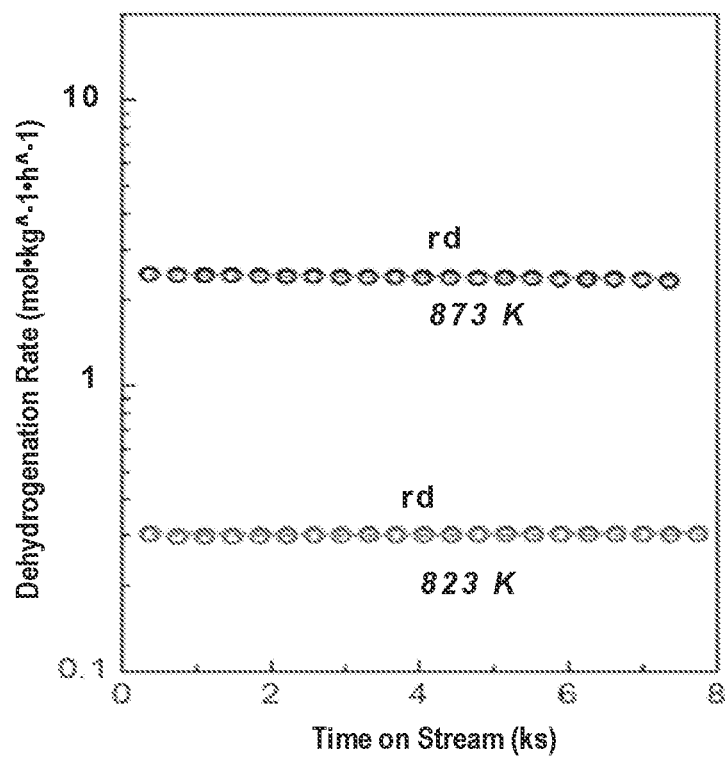
FIG. 4 shows the dehydrogenation rate per mass of catalyst with additional $H_2$ present ($r_d$) during a PDH reaction on a $ZrO_2$ catalyst with $O_2$/He pretreatment at different temperatures.

Prior to the PDH reaction, the catalyst was pretreated in O$_2$/He at corresponding temperatures corresponding the PDH reaction temperatures (i.e., 823 K, 873 K). As the H$_2$ was co-fed into the reaction gas stream comprising C$_3$H$_8$, an inhibition effect on dehydrogenation rate was observed at 823 K. As shown in FIG. 4, the initial dehydrogenation rate at 823 K decreased from 0.7 mol kg$^{-1}$ h$^{-1}$ to 0.31 mol kg$^{-1}$ h$^{-1}$. Also shown in FIG. 4, the initial dehydrogenation rate at 873 K decreased from 5.2 mol kg$^{-1}$ h$^{-1}$ to 2.5 mol kg$^{-1}$ h$^{-1}$.

It was also found that there was no contribution to the cracking rate from the ZrO$_2$ catalyst during the PDH reaction with the additional H$_2$ at a pressure of 12.3 kPa at temperatures of 823 K and 873 K. The lack of contribution to the cracking rate at 873 K indicates that co-feeding with H$_2$ can improve the selectivity of the ZrO$_2$ catalyst towards C$_3$H$_8$.

The stability of the ZrO$_2$ catalyst improved in the PDH reaction when additional H$_2$ was co-fed with the propane at a pressure of 12.3 kPa and a temperature of 873 K. Indeed, the catalyst half-life was 46 h as compared to 0.28 h during the PDH reaction at 873 K without co-feeding with H$_2$. At 823 K, there was no observable deactivation during the PDH reaction under the presence of additional H$_2$ at a pressure of 12.3 kPa. Because H$_2$ pretreatment can activate the catalyst as demonstrated in Example 3, it is possible that by co-feeding H$_2$ during the PDH reaction, Zr$_{cus}$ surface-active sites may be generated or maintained continuously so that any formation of carbonaceous species does not affect the catalytic activity.

Figure 5:
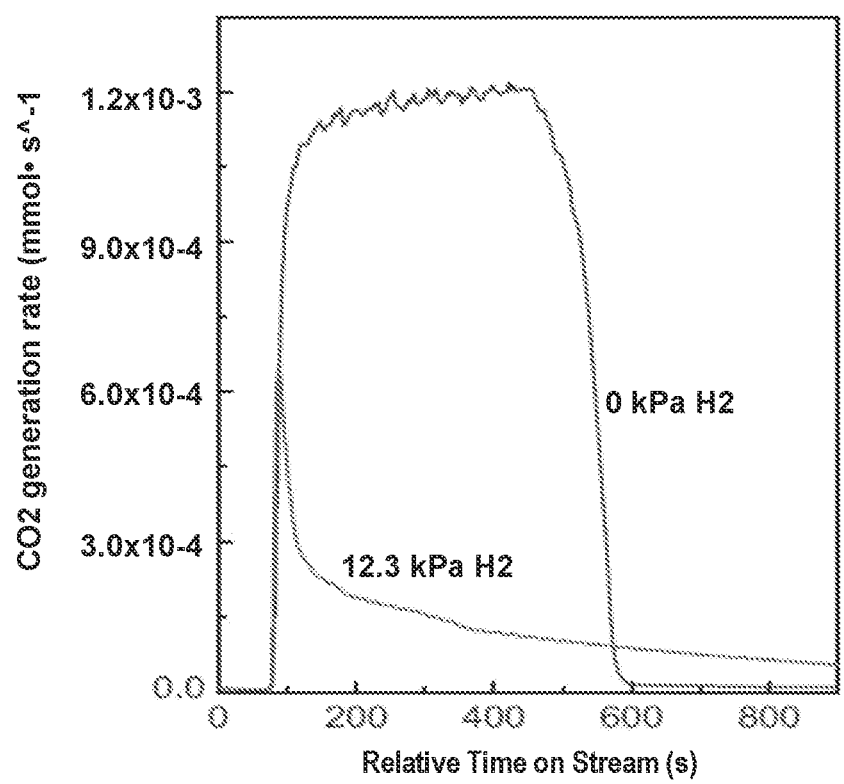
FIG. 5 shows the $CO_2$ generation rate during a re-oxidation process after a PDH reaction with and without the presence of additional $H_2$ at 873 K on $ZrO_2$ catalyst.

FIG. 5 shows the CO$_2$ generation rate during a re-oxidation process after a PDH reaction with and without the presence of additional H$_2$ at 873 K on the ZrO$_2$ catalyst. During the re-oxidation, a mixture of 4% O$_2$/He was provided at a rate of 2 cm$^3$ g$^{-1}$ s$^{-1}$ and a temperature of 873 K. By comparing the total amount of CO$_2$ generated during the re-oxidation process, it was found that by co-feeding the H$_2$ with the propane feed gas, the formation of carbonaceous species could be inhibited.

After the PDH reaction at 873 K on the ZrO$_2$ catalyst pretreated with O$_2$/He, the total amount of CO$_2$ generated during the subsequent re-oxidation process was 2.6 mmol g$_{cat}^{-1}$, which corresponds to a surface carbon density of 35 C-atoms/nm$^2$. Considering the surface Zr—O pair density of 7 nm$^{-2}$, the formation of carbonaceous species is likely to cover the active sites on ZrO$_2$ catalyst surface, which can eventually lead to deactivation. After the PDH reaction with additional 12.3 kPa H$_2$ at 873 K on ZrO$_2$ catalyst with O$_2$/He pretreatment, only 0.5 mmol g$_{cat}^{-1}$ CO$_2$ was generated during subsequent re-oxidation process, which corresponds to a surface carbon density of 6.6 nm$^{-2}$ (FIG. 5). The presence of additional H$_2$ at a pressure of 12.3 kPa during the PDH reaction at 873 K, led to a greater than five-fold decrease in the surface density of carbonaceous species as compared to the PDH reaction at 873 K without additional H$_2$. Together with the observed activation effect on the ZrO$_2$ catalyst during the PDH reaction after H$_2$ pretreatment, the stabilization of ZrO$_2$ during the PDH reaction by co-feeding H$_2$ may be attributable to continuous generation of surface-active sites while the formation of carbonaceous species is effectively inhibited. Without being bound by any particular theory, these data seem to indicate that the role of H$_2$ is to continuously remove the C as it forms at a rate higher than that achieved by the H$_2$ formed in situ by the dehydrogenation reaction. These two effects of pre-treatment and co-feeding with H$_2$ lead to a stable ZrO$_2$ catalyst during the PDH reaction with high selectivity towards propene.

Examide 5—Dependence of Dehydrogenation Rate on H$_2$ and C$_3$H$_8$

Figure 6:
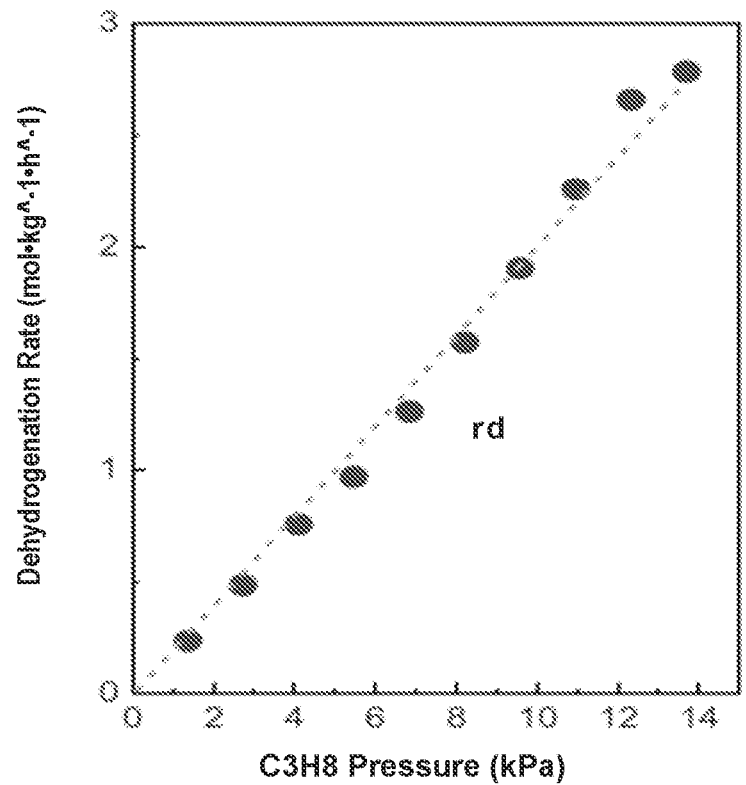
FIG. 6 shows the dehydrogenation rate per mass of catalyst ($r_d$) during a PDH reaction.

The dependence of the dehydrogenation rate on H$_2$ and C$_3$H$_8$ was evaluated. The dehydrogenation rate per mass of catalyst ($r_d$) was determined during a PDH reaction with additional H$_2$ at a pressure of 12.3 kPa and a temperature of 873 K on the ZrO$_2$ catalyst as a function of C$_3$Ha partial pressure. Due to the stabilization effect on the activity of the ZrO$_2$ catalyst during the PDH reaction with additional H$_2$, the dependence of the dehydrogenation rate on the partial pressure of C$_3$H$_8$ could be accurately determined at 873 K under the presence of additional H$_2$ at a pressure of 12.3 kPa for a ZrO$_2$ catalyst pretreated in O$_2$/He at 873 K. As shown in FIG. 6, the dehydrogenation rate increased proportionally with increasing C$_3$H$_8$ partial pressure while there was no contribution to cracking rate from the ZrO$_2$. This trend indicates that at 873 K the PDH reaction occurs on the surface with low coverages of C$_3$H$_8$-derived species, which are either weakly-bound or scavenged in fast subsequent reactions after they formed.

FIG. 7A shows the dehydrogenation rate per mass of catalyst (r$_d$) during a PDH reaction where the propane gas was co-fed with H$_2$ at a pressure of 12.3 kPa or 24.6 kPa and a temperature of 823 K on the ZrO$_2$ catalyst as a function of C$_3$H$_8$ partial pressure. FIG. 7B shows the dehydrogenation rate per mass of catalyst (r$_d$) during the PDH reaction where the propane gas was introduced at a pressure of 4.1 kPa, 13.7 kPa and 30.1 kPa and a temperature of 823 K on the ZrO$_2$ catalyst as a function of H$_2$ partial pressure.

The dependence of dehydrogenation rate on C$_3$H$_8$ and H$_2$ partial pressure at 823 K was determined for a ZrO$_2$ catalyst pretreated in O$_2$/He at 823 K. Under 12.3 kPa of additional H$_2$, an inhibition of dehydrogenation rate at elevating C$_3$H$_8$ partial pressure was observed at 823 K. This indicates that under additional H$_2$ at a pressure of 12.3 kPa, the catalyst surface has become saturated with C$_3$H$_8$-derived intermediates at high C$_3$H$_8$ partial pressure (FIG. 7A), which can inhibit the dehydrogenation rate.

As the partial pressure of additional H$_2$ increased to 24.6 kPa, the dehydrogenation rate increased proportionally with increasing C$_3$H$_8$ partial pressure at 823 K, indicating that under additional H$_2$ at a pressure of 24.6 kPa, the C$_3$H$_8$-derived intermediates can undergo fast subsequent reaction on the catalyst surface and the dehydrogenation rate will not be inhibited. No contribution to cracking rate from the ZrO$_2$ was observed during the above mentioned PDH reaction under 12.3 kPa and 24.6 kPa of additional H$_2$.

As shown in FIG. 7B, the dependence of dehydrogenation rate on H$_2$ partial pressure was studied under 4.1 kPa, 13.7 kPa and 30.1 kPa C$_3$H$_8$ at 823 K. An inhibition effect on the dehydrogenation rate was observed for all three C$_3$H$_8$ partial pressures at increasing H$_2$ partial pressure and the dehydrogenation rate eventually became constant with an H$_2$ partial pressure higher than 58 kPa. There are two possible origins for the H$_2$ inhibition effect: 1) either the additional H$_2$ is reversing the C—H bond activation step by reacting with the formed alkyl group to re-form C$_3$H$_8$; or 2) it is increasing the H-content of the carbonaceous deposit and making it less willing to accept hydrogen from C$_3$H$_8$.

Example 6—Benchmark of PDH Activity on Different ZrO$_2$ Catalysts

A benchmark of the PDH reaction activity on different ZrO$_2$ catalysts was determined. The dehydrogenation rate of propane on ZrO$_2$ catalysts as prepared in Example 1 according to various embodiments was compared with the PDH activity data on ZrO$_2$ from previous studies (FIG. 8). FIG. 8 shows a comparison of initial dehydrogenation rate of propane among ZrO$_2$ catalysts in current research: a) ZrO$_{2c}$ dehydrogenation rate after the catalyst has been pretreated in 4 kPa O$_2$, He balance; b) the dehydrogenation rate after the catalyst been regenerated in 4 kPa O$_2$, He balance, and c) from references ZrO$_{2r-1}$, ZrO$_{2r-2}$ and ZrO$_{2r-3}$. The PDH reaction was operated with C$_3$H$_8$ at a pressure of 40 kPa and a temperature of 823K.

The ZrO catalysts from previous studies were commercial ZrO$_2$ (by Saint-Gobain) with different crystalline sizes (ZrO$_2{}^r$-1: 43 nm, ZrO$_2{}^r$-2: 13 nm, ZrO$_2{}^r$-3: 9 nm). The dehydrogenation rate at 823 K on the commercial ZrO$_2$ catalyst increased with decreasing crystalline size, but the selectivity towards propene decreased with decreasing crystalline size. For the ZrO$_2{}^r$-3 catalyst with a crystalline size of 9 nm, the selectivity towards propene was 98%. For the ZrO$_2$ catalyst as prepared in Example 1 according to embodiments herein, the dehydrogenation rate at 823 K was higher than that on ZrO$_2{}^r$-1 and the PDH reaction was highly selective towards propene (no contribution to cracking rate from ZrO$_2$ was observed after the subtraction of gas phase activity). After the PDH reaction, the ZrO$_2$ catalyst prepared in accordance with Example 1 and embodiments herein, was treated in 4 kPa O$_2$ at 823 K for 30 min and the subsequent PDH reaction after regeneration exhibited a dehydrogenation rate comparable with the first PDH activity measurement (FIG. 8), which indicates the ZrO$_2$ catalyst can be fully regenerated by oxidative treatment. This observation is consistent with previous studies where several PDH reaction-regeneration cycles were performed on ZrO$_2$ at 823 K and no decrease in initial dehydrogenation rate was observed.

The introduction of additional H$_2$ during the PDH reaction on ZrO$_2$ catalyst provided a method to improve the stability of the catalyst through an inhibition of the formation of inactive carbonaceous species. This inhibition can lead to higher stability of the catalyst. No contribution to cracking rate from the ZrO$_2$ catalyst when additional H$_2$ was present during the PDH reaction at 873 K and all cracking products detected can be fully attributed to homogenous reactions that occur even in an empty reactor. This method may provide a general strategy to improve the stability of oxide-based catalyst during paraffin dehydrogenation reaction.

The preceding description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail in order to avoid unnecessarily obscuring the present invention. Thus, the specific details set forth are exemplary. Particular embodiments may vary from these exemplary details and still be contemplated to be within the scope of the present invention.

Although the operations of the methods herein are described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

It is to be understood that the above description is intended to be illustrative, and not restrictive. Many other embodiments will be apparent to those of skill in the art upon reading and understanding the above description. The scope of the invention should, therefore, be determined with reference to the appended claims, along with the full scope of equivalents to which such claims are entitled.

We claim:

1. A catalyst composition, comprising:
zirconium oxide (ZrO$_2$), wherein the catalyst composition is free of at least one of chromium or a precious metal, wherein the catalyst composition has been pretreated by contacting the catalyst composition with a pretreatment gas comprising a reducing agent at a concentration of about 1 mol % to about 10 mol %, and wherein the reducing agent comprises at least one of hydrogen ($H_2$), carbon monoxide (CO), ammonia or methane ($CH_4$).

2. The catalyst composition of claim 1, comprising at least about 50 wt % $ZrO_2$ based on total weight of the catalyst composition.

3. The catalyst composition of claim 1, comprising a plurality of $Zr_{cus}$ surface-active sites.

4. The catalyst composition of claim 1, wherein the $ZrO_2$ comprises at least one of a monoclinic phase of $ZrO_2$ or a tetragonal phase of $ZrO_2$.

5. The catalyst composition of claim 1, comprising a BET surface area of about 1 $m^2$ $g^{-1}$ to about 100 $m^2$ $g^{-1}$.

6. The catalyst composition of claim 1, further comprising a rare earth metal comprising at least one lanthanide metal, an oxide thereof or combinations thereof.

7. The catalyst composition of claim 1, further comprising about 0.5 wt % to about 50 wt % of a rare earth metal comprising at least one of yttrium (Y), erbium (Er), cerium (Ce), dysprosium (Dy), gadolinium (Gd), lanthanum (La), neodymium (Nd), samarium (Sm), ytterbium (Yb), oxides thereof or mixtures thereof.

8. The catalyst composition of claim 1, further comprising yttria, wherein an atomic ratio of Y:Zr is from greater than 0 to about 0.2.

9. The catalyst composition of claim 8, comprising a BET surface area of about 40 $m^2$ $g^{-1}$ to about 110 $m^2$ $g^{-1}$.

10. The catalyst composition of claim 1, wherein the catalyst composition has been pretreated and comprises more surface-active sites than before pretreatment.

11. The catalyst composition of claim 1, comprising a plurality of units, wherein the plurality of units comprise at least one of particles, powder, extrudates, tablets, agglomerates, granules, spheres or combinations thereof.

12. The catalyst composition of claim 11, wherein the plurality of units comprise a mean size of about 1.5 mm to about 5.0 mm.

13. The catalyst composition of claim 11, wherein the plurality of units comprise a mean size of about 100 μm to about 250 μm.

14. A kit comprising:
a catalyst composition comprising zirconium oxide ($ZrO_2$), wherein the catalyst composition is free of at least one of chromium or a precious metal; and
at least one of:
(A) instructions for pretreating the catalyst composition, comprising:
contacting the catalyst composition with a pretreatment gas, wherein the pretreatment gas comprises a reducing agent at a concentration of about 1 mol % to about 10 mol %, and wherein the reducing agent comprises at least one of hydrogen ($H_2$), carbon monoxide (CO), ammonia or methane ($CH_4$); or
(B) instructions for using the catalyst composition, comprising:
dehydrogenating a light alkane gas, comprising combining hydrogen ($H_2$) with the light alkane gas in the presence of the catalyst composition.

15. A catalyst composition, comprising:
zirconium oxide ($ZrO_2$), wherein the catalyst composition is free of at least one of chromium or a precious metal, wherein the catalyst composition is in the form of a plurality of units, wherein the plurality of units comprise at least one of particles, powder, extrudates, tablets, agglomerates, granules, spheres or combinations thereof, and wherein the plurality of units comprise a mean size of about 1.5 mm to about 5.0 mm.

* * * * *